United States Patent [19]

Le Gigan

[11] Patent Number: 5,332,307
[45] Date of Patent: Jul. 26, 1994

[54] MEASUREMENT CELL FOR GRANULAR OR POWDERED PRODUCTS

[75] Inventor: Dominique Le Gigan, Parmain, France

[73] Assignee: Star Partners, Chicago, Ill.

[21] Appl. No.: 124,352

[22] Filed: Sep. 20, 1993

Related U.S. Application Data

[63] Continuation of Ser. No. 897,270, Jun. 11, 1992, abandoned.

[30] Foreign Application Priority Data

Jun. 11, 1992 [FR] France ................................ 91 07217

[51] Int. Cl.⁵ .......................................... G01R 27/02
[52] U.S. Cl. .................................................. 324/664
[58] Field of Search .................. 73/73, 433, 435, 436, 73/863.41, 863.44, 864.51, 866, 863.42, 863.43, 863.45, 863.54–863.56, 863.91, 863.92; 324/663–670, 664; 99/487; 206/305; 220/558; 128/34.1, 34.4, 34.5; 217/122–125

[56] References Cited

U.S. PATENT DOCUMENTS

| D. 55,289 | 5/1920 | Loewenberg | 217/124 |
|---|---|---|---|
| 226,854 | 4/1880 | Hogg | 217/123 |
| 276,377 | 4/1883 | Ferguson | 217/124 |
| 565,460 | 8/1896 | Hourdeaux | 217/125 |
| 2,076,861 | 4/1937 | Parsons | 73/863.41 |
| 3,721,179 | 3/1973 | Applegate . | |
| 3,781,673 | 12/1973 | Resh | 324/670 |
| 3,794,911 | 2/1974 | Fathauer | 324/665 |
| 4,107,599 | 8/1978 | Preikschat | 324/670 |
| 4,168,466 | 9/1979 | Boldt | 324/664 |
| 4,193,116 | 3/1980 | Funk . | |
| 4,487,278 | 12/1984 | Rosenthal | 73/433 |

FOREIGN PATENT DOCUMENTS

| 1121378 | 1/1956 | Fed. Rep. of Germany | 324/663 |
|---|---|---|---|
| 778157 | 3/1935 | France . | |
| 2558282 | 7/1985 | France . | |
| 56-150329 | 11/1981 | Japan . | |
| WO89/10548 | 11/1989 | PCT Int'l Appl. . | |
| 0687368 | 9/1979 | U.S.S.R. | 73/863.44 |

OTHER PUBLICATIONS

English Abstract of Japanese application 56-150329, Patent Abstracts of Japan, vol. 6030, (Feb. 23, 1982).

*Primary Examiner*—Robert Raevis
*Attorney, Agent, or Firm*—Willian Brinks Hoffer Gilson & Lione

[57] ABSTRACT

The invention relates to a measurement cell for granular or powdered products, including a fill opening in its upper portion. A cell according to the invention is remarkable in particular in that the plane of its fill opening, in the operational position, forms an acute dihedral angle with a horizontal plane in order by gravitation to limit the size of the dome formed by the product after filling. A cell according to the invention has numerous applications and may in particular be intended for measuring the moisture content of cereals, deaginous, or proteaneceous.

19 Claims, 1 Drawing Sheet

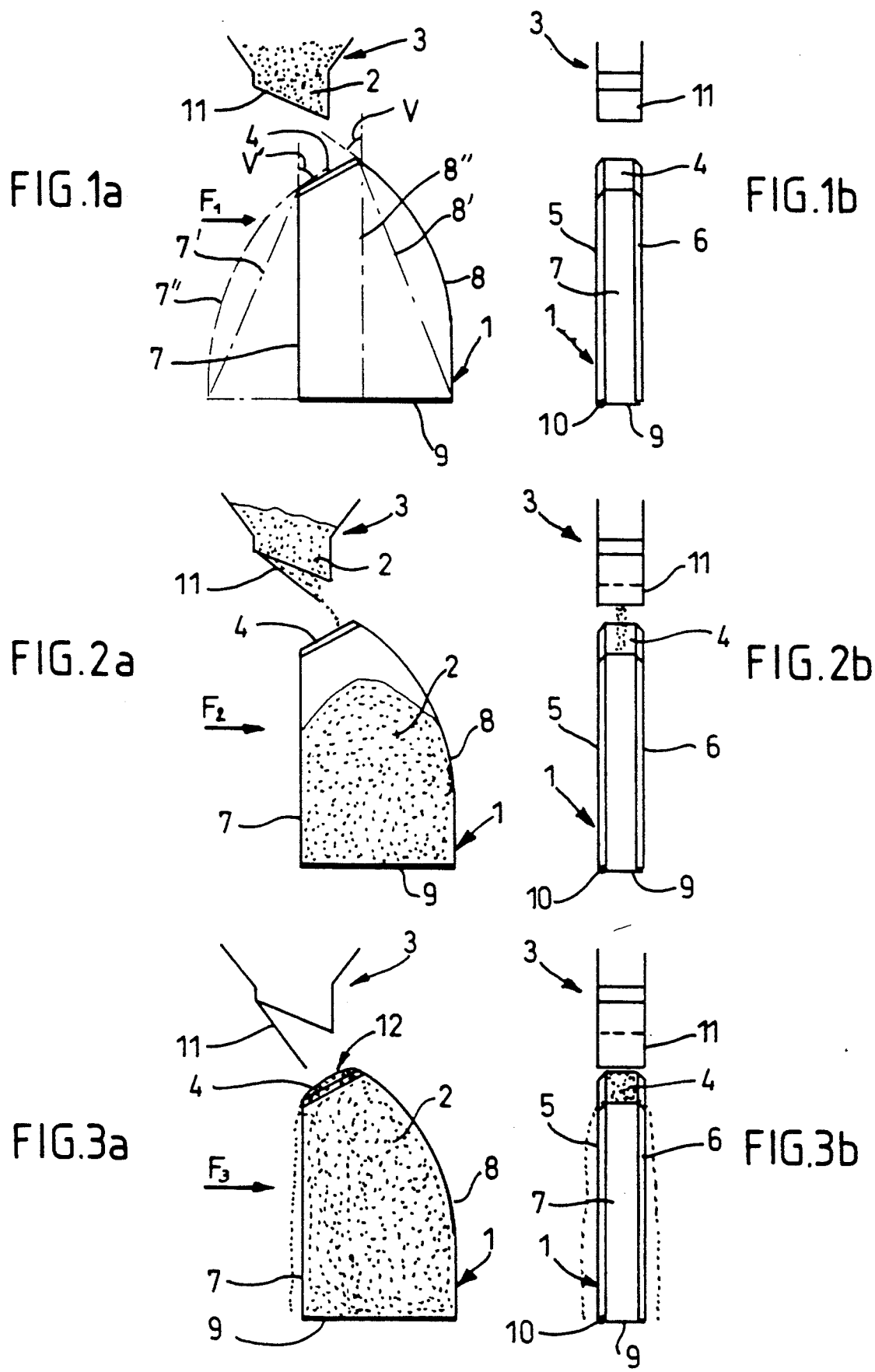

MEASUREMENT CELL FOR GRANULAR OR POWDERED PRODUCTS

This application is a continuation of application Ser. No. 07/897,270, filed Jun. 11, 1992, now abandoned.

Applicant claims, under 35 U.S.C. §119, the benefit of priority of the filing date of Jun. 13, 1991, of a French application, copy attached, Serial Number 9107217, filed on the aforementioned date, the entire contents of which are incorporated herein by reference.

FIELD OF THE INVENTION

The invention relates to a measurement cell for granular or powdered products. The measurement cell can be used for measuring the contents of certain substances in a product or for measuring the moisture content in cereals or the like.

BACKGROUND OF THE INVENTION

For repetitive, constant filling of a container-like cell, with a granular or powdered product, the product must be made level, or substantially level. However, in the vicinity of the opening of the cell, the product generally forms a dome. One disadvantage of the formation of a dome is that its size and volume may vary, particularly as a function of the characteristics of the product. Thus, a measurement such as the test weight or moisture will be inaccurate.

For this reason, systems with sweeping arms to eliminate the dome have been conceived of and an example of which is described in French Patent 2389179 (corresponding to U.S. Pat. No. 4,193,116). Such systems require mechanical movement means and have the disadvantages of being costly and having an inherent risk of breaking down.

OBJECT AND SUMMARY OF THE INVENTION

To overcome these disadvantages, the inventor has conceived of a self-leveling measurement cell that works simply by gravity. In an operational position of the cell, a fill opening of the cell forms an acute dihedral angle with respect to a horizontal plane, which results in gravity limiting the size of the dome formed by the product after filling.

In one embodiment, the cell comprises a rectangular opening. The rectangular opening has two opposite and inclined sides and two horizontal sides. The cell further includes two lateral plane and parallel walls connected to the two opposite and inclined sides of the opening and two other walls connected to the other two horizontal sides of the opening. The two lateral plane and parallel walls and the two other walls further extend from the opening to the base of the cell.

Moreover, in another embodiment, the opening may be of generally trapezoidal shape, whose bases are horizontal and joined to plane and parallel walls, while the sides (at least one of which may be curved) are connected to inclined or inwardly curved walls. Contrarily to the above embodiments, it will be understood that the plane and parallel walls are then connected to the horizontal sides.

A cell according to the invention has multiple applications and various measurement sensors may be associated with the cell. For example, the cell may be used for the capacitive measurement of the moisture content of cereals. In this embodiment, the two plane and parallel walls of the cell constitute the plates of the measurement capacitor, for example.

The invention will be better understood and further features thereof will become more apparent from the ensuing detailed description, taken in conjunction with the accompanying drawings.

BRIEF DESCRIPTION OF THE DRAWINGS

FIGS. 1a–3a are schematic elevation views of a measurement cell according to one embodiment of the invention taken before filling, during filling and at the end of filling of a granular or powder product, respectively; and FIGS. 1b–3b are views taken along the arrows $F_1$, $F_2$ and $F_3$ of the respective FIGS. 1a–3a.

DESCRIPTION OF THE PREFERRED EMBODIMENT

In the drawings, a measurement cell 1 can be seen in an operational position, intended for receiving a granular or powdered product 2 initially contained in a feed hopper 3 disposed just above the cell 1.

As seen in FIGS. 1b, 2b, and 3b, the cell 1 includes an opening 4, which is rectangular. Rectangular opening 4 is disposed along an inclined plane which forms an acute, preferably a dihedral angle of less than or equal to 45° with respect to a horizontal plane parallel to a base 9 of the cell. Thus, the short opposed sides of the rectangular opening are horizontal while the long sides are inclined with respect to the horizontal plane.

In the embodiment shown, it can also be seen that the opening 4 occupies the entire surface area of the upper portion of the cell 1.

The cell 1 also includes two lateral walls 5 and 6 which are planar and parallel to each other as shown in FIGS. 1b, 2b and 3b. The walls 5 and 6 are connected to the two long opposed and inclined sides of the opening 4. Walls 7 and 8 are also connected to the other two short horizontal opposed sides of the opening 4. Wall 7 is connected to the side lower level and wall 8 is connected to the horizontal side located at the higher level.

The four walls 5, 6, 7 and 8 meet a base 9 opposite the opening 4 and parallel to the horizontal plane. The base 9 of the cell is for instance constituted by a trap door articulated for rotation about an axis or shaft 10 (FIGS. 1b, 2b, 3b), to permit the evacuation of the cell.

As the drawings also show, the wall 7 is vertical with respect to the horizontal plane, while the wall 8 is curved inward from a certain height toward opposing wall 7. This shape is especially advantageous but is not obligatory.

In FIG. 1a (before filling), two other possible forms 7' and 7" (inclined and curved inward, respectively) for the wall 7 and two other forms 8' and 8" (respectively inclined and vertical) for the wall 8 have been shown in dot-dash lines. All the combinations are clearly possible, and others may also be imagined, especially if the opening 4 does not occupy the entire upper portion of the cell 1, unlike the embodiment shown.

It is also clear that the short sides of the rectangular opening may be inclined sides, and the long sides may be the horizontal ones. Furthermore, the opening may be circular, elliptical, trapezoidal, or of some other shape. Similarly, as already noted, the planar walls 5 and 6 may be connected to two horizontal sides of the opening 4, and one or both of the inclined or inwardly curved walls may be joined to the inclined sides of the opening 4.

Despite the various shapes available for the cell, it has been discovered that the embodiments shown in FIGS. 2a and 3a facilitate complete filling of the cell and maximize its useful volume, while minimizing the volume of the residual dome 12 of the product.

The drawings show a feed hopper 3 provided with an opening door 11 that is inclined in a conventional manner. The inclination of the flap 11 is opposite that of the opening 4, while the wall 8 is curved inward in the direction of flow of the product 2 as shown in FIG. 2a. However, in the case where the planar walls are connected to the horizontal sides of the opening 4 and the inclined or inwardly curved walls are connected to the inclined sides, the second aforementioned characteristic disappears while the first is maintained, that is, the inclination of the door 11 opposite that of the opening 4.

At the end of filling of the cell, that is, until the product 2 overflows, the product 2 forms a slight dome 12 above the opening 4 where the size of the dome is limited because the opening 4 is inclined. For various reasons, the slope of opening 4 is advantageously less than 45°, for example being 30°. In that case, since the dome is small, the variations in the volume of the dome during successive fillings are particularly slight.

For good filling of the cell 1, it is also advantageous that the plane at a tangent to the inwardly curved wall containing the horizontal side of the opening 4 to which this inwardly curved wall is connected, forms with the vertical a sufficiently acute angle V,V', for example less than 70° and in particular 60°.

To assure better overflow of the excess product during the filling, at least some of the edges of the opening 4 are chamfered, as FIGS. 1b, 2b and 3b show for the inclined edges of this opening.

In the embodiment described, in order to constitute a cell for measuring the moisture content of the product by capacitive means (aside from other measurements, such as of the test weight, and so forth), the lateral plane walls 5 and 6 advantageously constitute the plates of the measurement capacitor.

Advantageously, the fill opening of the cell is open over the entire surface area of the upper portion of the cell.

Preferably, the horizontal section of the cell decreases at least in part from the base of the cell toward its opening. In this case, at least one of the walls, joined to one of the horizontal sides of the opening, and which begins at the base of the cell, is preferably inclined at least in part toward the opposite wall, which in turn is connected to the other, horizontal side of the opening. Instead of being inclined, this wall may advantageously be curved inward. Furthermore, if one of the aforementioned two walls may be inclined or curved inward, preferably the one that is connected to the horizontal side of the opening, at a higher level, then clearly both walls may also be inclined or curved inward.

The invention may be embodied in other forms than those specifically disclosed herein without departing from its spirit or essential characteristics. The described embodiments are to be considered in all respects only as illustrative and not restrictive, and the scope of the invention is commensurate with the appended claims rather than the foregoing description.

I claim:

1. A measurement cell for measuring granular or powdered products, comprising:
   a base located at a lower portion of the measurement cell;
   a fill opening located in an upper portion of the measurement cell, wherein the fill opening comprises two opposite and inclined sides and the fill opening defines a plane and which forms an acute dihedral angle with a horizontal plane when the measurement cell is in an operational position;
   a middle portion of the measurement cell connected to said base and said fill opening, wherein said middle portion comprises two lateral plane and parallel wall connected to the two opposite and inclined sides of the opening and defines horizontal cross-sections taken parallel to said horizontal plane which vary in size continuously from said base to said fill opening, thereby limiting the size of the dome formed by the products after filling due to the force of gravity; and
   wherein said two plane and parallel walls of said cell comprise plates of a measurement capacitor for capacitive measurement of the moisture content of cereals, oleaginous or proteaneceous products.

2. The measurement cell of claim 1, wherein the acute dihedral angle formed between the plane of the opening and the horizontal plane is less than or equal to 45°.

3. The measurement cell of claim 2, wherein the fill opening of the measurement cell is open over the entire surface area of the upper portion of said measurement cell.

4. The measurement cell of claim 3, wherein the horizontal sections decrease in size from the base toward the opening in the operational position.

5. The measurement cell of claim 4, said opening having a rectangular shape and having two horizontal sides;
   said middle portion comprising two other walls connected to the other two horizontal sides of said opening, wherein said two other walls further extend from said opening to the base of the cell.

6. The measurement cell of claim 5, wherein at least one of the two other walls is joined to one of the other two horizontal sides of the opening, and which begins at the base of the cell, is at least in part inclined toward the opposite other wall, which in turn is connected to the other horizontal side of the opening.

7. The measurement cell of claim 5, wherein at least one of the two other walls is joined to one of the other two horizontal sides of the opening, and which begins at the base of the cell, is at least in part curved inward toward the opposite other wall, which in turn is connected to the other horizontal side of the opening.

8. The measurement cell of claim 7, comprising a plane tangent to the inwardly curved wall containing the horizontal side of the opening to which said inwardly curved wall is connected forms an angle with the vertical that is less than 70°.

9. The measurement cell of claim 8, wherein said opening of the cell comprises chamfered edges to assure a better overflow of any excess product.

10. The measurement of claim 1, wherein the fill opening of the measurement cell is open over the entire surface area of the upper portion of said measurement cell.

11. The measurement cell of claim 1, wherein the horizontal sections decrease in size from the base toward the opening in the operational position.

12. The measurement cell of claim 1, said opening having a rectangular shape and having two horizontal sides;

said middle portion comprising two other walls connected to the other two horizontal sides of said opening, wherein said two other walls further extend from said opening to the base of the cell.

13. The measurement cell of claim 12, wherein at least one of the two other walls is joined to one of the other two horizontal sides of the opening, and which begins at the base of the cell, is at least in part inclined toward the opposite other wall, which in turn is connected to the other horizontal side of the opening.

14. The measurement cell of claim 12, wherein at least one of the two other walls is joined to one of the other two horizontal sides of the opening, and which begins at the base of the cell, is at least in part curved inward toward the opposite other wall, which in turn is connected to the other horizontal side of the opening.

15. The measurement cell of claim 14, comprising a plane tangent to the inwardly curved wall containing the horizontal side of the opening to which said inwardly curved wall is connected forms an angle with the vertical that is less than 70°.

16. The measurement cell of claim 1, wherein said opening of the cell comprises chamfered edges to assure a better overflow of any excess product.

17. A measurement cell for measuring granular or powdered products, comprising:
a base located at a lower portion of the measurement cell;
a fill opening located in an upper portion of the measurement cell and is open over the entire surface area of the upper portion of the measurement cell, wherein the fill opening comprises a rectangular shape having two horizontal sides and two opposite and inclined sides and the fill opening defines a plane and which forms an acute dihedral angle of less than or equal to 45° with a horizontal plane when the measurement cell is in an operational position;
a middle portion of the measurement cell connected to said base and said fill opening wherein said middle portion comprises two lateral plane and parallel walls connected to the two opposite and inclined sides of the opening and two other walls connected to the other two horizontal sides of said opening, wherein said two lateral plane and parallel walls and said two other walls further extend from said opening to the base of the cell, and wherein said middle portion in the operational position defines horizontal cross-sections taken parallel to said horizontal plane which decrease in size continuously from said base to said fill opening, thereby limiting the size of the dome formed by the products after filling due to the force of gravity;
wherein at least one of the two other walls is joined to one of the other two horizontal sides of the opening, and which begins at the base of the cell, is at least in part inclined toward the opposite other wall, which in turn is connected to the other horizontal side of the opening; and
wherein said two plane and parallel walls of said cell comprise plates of a measurement capacitor for capacitive measurement of the moisture content of cereals, oleaginous or proteaneceous products.

18. A measurement cell for measuring granular or powdered products, comprising:
a base located at a lower portion of the measurement cell;
a fill opening located in an upper portion of the measurement cell and is open over the entire surface area of the upper portion of the measurement cell, wherein the fill opening comprises a rectangular shape having two horizontal sides and two opposite and inclined sides and the fill opening defines a plane and which forms an acute dihedral angle of less than or equal to 45° with a horizontal plane when the measurement cell is in an operational position;
a middle portion of the measurement cell connected to said base and said fill opening, wherein said middle portion comprises two lateral plane and parallel walls connected to the two opposite and inclined sides of the opening and two other walls connected to the other two horizontal sides of said opening, wherein said two lateral plane and parallel walls and said two other walls further extend from said opening to the base of the cell, and wherein said middle portion in the operational position defines horizontal cross-sections taken parallel to said horizontal plane which decrease in size continuously from said base to said fill opening, thereby limiting the size of the dome formed by the products after filling due to the force of gravity;
wherein at least one of the two other walls is joined to one of the other two horizontal sides of the opening, and which begins at the base of the cell and is at least in part curved inward toward the opposite other walls, which in turn is connected to the other horizontal side of the opening, wherein there is a plane tangent to the part curved inward and forms an angle with the vertical that is less than 70° and said opposite other wall is connected to the other horizontal side of the opening,
wherein said two plane and parallel walls of said cell comprise plates of a measurement capacitor for capacitive measurement of the moisture content of cereals, oleaginous or proteaneceous products.

19. A measurement cell for measuring granular or powdered products, comprising:
a base located at a lower portion of the measurement cell;
a fill opening located in an upper portion of the measurement cell, wherein the fill opening comprises a rectangular shape having two horizontal sides and two opposite and inclined sides and the fill opening defines a plane and which forms an acute dihedral angle with a horizontal plane when the measurement cell is in an operational position;
a middle portion of the measurement cell connected to said base and said fill opening, wherein said middle portion comprises two lateral plane and parallel walls connected to the two opposite and inclined sides of the opening and two other walls connected to the other two horizontal sides of said opening, wherein said two other walls further extend from said opening to the base of the cell, and wherein said middle portion defines horizontal cross-sections taken parallel to said horizontal plane which vary in size continuously from said base to said fill opening, thereby limiting the size of the dome formed by the products after filling due to the force of gravity; and
wherein said two plane and parallel walls of said cell comprise plates of a measurement capacitor for capacitive measurement of the moisture content of cereals, oleaginous or proteaneceous products.

* * * * *

UNITED STATES PATENT AND TRADEMARK OFFICE
CERTIFICATE OF CORRECTION

PATENT NO. : 5,332,307
DATED : July 26, 1994
INVENTOR(S) : Dominique Le Gigan

Page 1 of 2

It is certified that error appears in the above-indentified patent and that said Letters Patent is hereby corrected as shown below:

On the Title Page    Item [57]

In column 1, under "Foreign Application Priority Data" please delete "Jun. 11, 1992" and substitute --Jun. 13, 1991--.

In column 2, line 1, under "Foreign Patent Documents" please delete "1/1956" and substitute --1/1962--.

In column 2, "Attorney, Agent, or Firm", delete "Hoffer" and substitute --Hofer--.

UNITED STATES PATENT AND TRADEMARK OFFICE
CERTIFICATE OF CORRECTION

PATENT NO. : 5,332,307
DATED : July 26, 1994
INVENTOR(S) : Dominique Le Gigan

It is certified that error appears in the above-indentified patent and that said Letters Patent is hereby corrected as shown below:

Column 4, line 10,    delete "wall" and substitute
--walls--.

Column 4, line 59,    after "measurement" insert
--cell--.

Column 6, line 29,    delete "walls" and substitute
--wall--.

Signed and Sealed this

Eighteenth Day of July, 1995

Attest:

BRUCE LEHMAN

Attesting Officer    Commissioner of Patents and Trademarks